United States Patent
Lee et al.

(10) Patent No.: US 11,026,615 B2
(45) Date of Patent: Jun. 8, 2021

(54) DRY ELECTRODE FOR DETECTING BIOSIGNAL AND METHOD FOR MANUFACTURING SAME

(71) Applicant: Y-BRAIN INC, Daejeon (KR)

(72) Inventors: Ki-Won Lee, Daejeon (KR); Cheon-Ju Ko, Yongin-si (KR); Jong-Min Jang, Hwaseong-si (KR); Byung-Gik Kim, Daegu (KR)

(73) Assignee: Y-BRAIN INC, Daejeon (KR)

( * ) Notice: Subject to any disclaimer, the term of this patent is extended or adjusted under 35 U.S.C. 154(b) by 345 days.

(21) Appl. No.: 15/960,027

(22) Filed: Apr. 23, 2018

(65) Prior Publication Data

US 2018/0235500 A1    Aug. 23, 2018

Related U.S. Application Data

(63) Continuation-in-part of application No. PCT/KR2016/011906, filed on Oct. 21, 2016.

(30) Foreign Application Priority Data

Oct. 22, 2015 (KR) .......................... 10-2015-0147472

(51) Int. Cl.
*A61B 5/291* (2021.01)
*A61L 31/16* (2006.01)
(Continued)

(52) U.S. Cl.
CPC ............ *A61B 5/291* (2021.01); *A61L 31/024* (2013.01); *A61L 31/041* (2013.01); *A61L 31/06* (2013.01);
(Continued)

(58) Field of Classification Search
CPC .................. A61B 5/0478; A61B 5/291; A61B 2562/0215; A61B 2562/125;
(Continued)

(56) References Cited

U.S. PATENT DOCUMENTS 4,033,334 A * 7/1977 Fletcher .................. A61B 5/25
 600/383
2001/0044573 A1* 11/2001 Manoli ................ A61B 5/6804
 600/383

(Continued)

FOREIGN PATENT DOCUMENTS

CN 104287727 A † 1/2015
JP 2003-520094 A 7/2003
(Continued)

OTHER PUBLICATIONS

International Search Report for corresponding international application PCT/KR2016/011906 dated Feb. 3, 2017.
(Continued)

*Primary Examiner* — Eun Hwa Kim
*Assistant Examiner* — Adam Z Minchella
(74) *Attorney, Agent, or Firm* — Hauptman Ham, LLP (57) ABSTRACT

Provided is a dry electrode for detecting a bio-signal, comprising a body part; a protrusion part formed on one surface of the body part; and a coating part formed on an end surface of the protrusion part, wherein the body part and the protrusion part comprise a conductive silicone, and the coating part comprises Ag, AgCl, and, optionally, 3-aminopropyltriethoxysilane.

19 Claims, 3 Drawing Sheets

(51) Int. Cl.
  *A61L 31/02* (2006.01)
  *A61L 31/04* (2006.01)
  *A61L 31/06* (2006.01)
  *A61L 31/08* (2006.01)
  *H01B 1/12* (2006.01)
  *H01B 5/14* (2006.01)
  *H01B 13/00* (2006.01)
  *A61N 1/04* (2006.01)

(52) U.S. Cl.
  CPC ............. *A61L 31/088* (2013.01); *A61L 31/16* (2013.01); *H01B 1/12* (2013.01); *H01B 5/14* (2013.01); *H01B 13/0036* (2013.01); *A61B 2562/0215* (2017.08); *A61B 2562/125* (2013.01); *A61L 2300/104* (2013.01); *A61L 2420/02* (2013.01); *A61L 2420/06* (2013.01); *A61N 1/0456* (2013.01)

(58) Field of Classification Search
  CPC ...... A61L 31/024; A61L 31/041; A61L 31/06; A61L 31/088; A61L 31/16; A61L 2300/104; A61L 2420/02; A61L 2420/06; H01B 1/12; H01B 5/14; H01B 13/0036; H01B 2562/0215; H01B 2562/125; A61N 1/0456
  See application file for complete search history.

(56) References Cited

U.S. PATENT DOCUMENTS

| | | |
|---|---|---|
| 2005/0261565 A1 | 11/2005 | Lane et al. |
| 2007/0225585 A1 | 9/2007 | Washbon et al. |
| 2012/0226127 A1* | 9/2012 | Asjes .................... A61B 5/0476 600/383 |
| 2014/0277318 A1 | 9/2014 | Richardson-Burns et al. |
| 2015/0157219 A1* | 6/2015 | Lee .................... A61B 5/02055 600/393 |
| 2016/0174859 A1* | 6/2016 | Oudenhoven ............ A61B 5/24 600/383 |
| 2018/0116546 A1* | 5/2018 | Pastoor .............. A61B 5/04087 |

FOREIGN PATENT DOCUMENTS

| | | | |
|---|---|---|---|
| JP | 2005-521458 A | | 7/2005 |
| JP | 2008-142541 A | | 6/2008 |
| JP | 2009-530064 A | | 8/2009 |
| KR | 10-2004-0095336 A | | 11/2004 |
| KR | 10-1539658 B1 | | 7/2015 |
| WO | WO/2000/045701 A1 | † | 8/2000 |
| WO | 0152731 A1 | | 7/2001 |
| WO | 03082104 A1 | | 10/2003 |
| WO | WO/2014/172775 A1 | † | 10/2014 |

OTHER PUBLICATIONS

Chen, Yun-Hsuan; Op de Beeck, Maaike; Carrette, Evelien; Vanderheyden, Luc; Grundlehner, Bernard; Mihajlovic, Vojkan; Boon, Paul; Van Hoof, Chris; "Polymer-based dry electrodes for high user comfort ECG/EEG measurements"; Conference Proceeding: 8th International Conference Exhibition on Integration Issues of Miniaturized Systems—MEMS, NEMS, ICs and Electronic Components; pp. 329-336; Mar. 26, 2014; Apprimus Verlag; Aachen, Germany.†

T. R. Mullen, C. Kothe, A. Ojeda; "Real-time Neuroimaging and Cognitive Monitoring Using Wearable Dry EEG"; IEEE Trans Biomed Eng, Nov. 2015; 61(11); pp. 2553-2567, doi: 10.1109/TBME.2015.2481482, published online Sep. 23, 2015.†

Chen Y.H., Op de Beeck M., Vanderheyden L., Mihajlovic V., Grundlehner B., Van Hoof C., "Comb-shaped Polymer-based Dry Electrodes for EEG/ECG Measurements with High User Comfort"; 35th Annual International Conference of the IEEE EMBS, Osaka, Japan, Jul. 3-7, 2013, pp. 551-554, IEEE (Piscataway, NJ), copyright 2013.†

Chi, Yu M.; "Advancements in Dry Electrode Technology for Medical Devices"; Lecture Slides from Presentation at the Department of Bioengineering of the University of California San Diego on Mar. 10, 2015; pp. 1-41; published Apr. 30, 2015; University of California San Diego, CA.†

\* cited by examiner
† cited by third party

DRY ELECTRODE FOR DETECTING BIOSIGNAL AND METHOD FOR MANUFACTURING SAME

CROSS REFERENCE TO RELATED APPLICATIONS

This application is a U.S. continuation-in-part application filed under 35 U.S.C. § 111(a), of International Application No. PCT/KR2016/011906, filed on Oct. 21, 2016, which claims priority to Korean Patent Application No. 10-2015-0147472 filed on Oct. 22, 2015, the disclosures of which are incorporated by reference.

TECHNICAL FIELD

The present disclosure relates to a dry electrode for detecting a bio-signal and a method for manufacturing the same.

BACKGROUND ART

A method of measuring the state of a brain includes an electroencephalogram (EEG) test in which a pad having an electrode is attached on the head to measure brainwaves received from the electrode; a CT test to examine a brain at various angles using radiation or ultrasound; an MRI test to scan a brain by magnetic resonance, etc.

In addition, in order to improve brain function and to treat persistent mental disorders, brain electrical stimulation techniques have been implemented using a transcranial direct current stimulation (tDCS) with a pad closely attached to the subject's head, or using a transcranial alternating current stimulation (tACS) in close contact with the subject's head.

Electrodes used in such devices for detecting a bio-signal are divided into wet electrodes and dry electrodes; in general, wet electrodes have been widely used due to their excellent performance in detecting a bio-signal. However, there is a need to develop a dry electrode in terms of ease of handling and use.

DISCLOSURE

Technical Problem

It is an aspect of the present invention to provide a dry electrode for detecting a bio-signal that is excellent in the performance of detecting the bio-signal.

Technical Solution

In one embodiment of the present disclosure, a dry electrode for detecting a bio-signal is provided, which may include a body part; a protrusion part formed on one surface of the body part; and a coating part formed on an end surface of the protrusion part, wherein the body part and the protrusion part may include a conductive silicone, and the coating part may include Ag and AgCl.

In one embodiment of the present disclosure, a dry electrode for detecting a bio-signal is provided, which may include a body part; a protrusion part formed on one surface of the body part; and a coating part formed on an end surface of the protrusion part, wherein the body part and the protrusion part may include a conductive silicone, and the coating part may include Ag, AgCl, and 3-aminopropyltriethoxysilane.

In one embodiment of the present disclosure, a method of manufacturing a dry electrode for detecting a bio-signal is provided, which may include the steps of: forming a body part having a protrusion part on one surface thereof to include a conductive silicone; and coating an end surface of the protrusion part to form a coating part comprising Ag and AgCl.

Advantageous Effects

The dry electrode for detecting a bio-signal is a dry electrode and can obtain a bio-signal at a level equivalent to that of a wet electrode, and therefore, the sensitivity of detecting a bio-signal is excellent, the time required is reduced, and the dry electrode is convenient to use.

BEST MODE

Hereinafter, exemplary embodiments of the present disclosure will be described in detail with reference to the accompanying drawings to the extent that those skilled in the art to which the present disclosure pertains can readily practice it. The present disclosure may be embodied in many different forms and is not limited to the embodiments described herein.

For clarity of the present disclosure, parts that are not relevant to the description are omitted, and the same or similar components are denoted by the same reference numerals throughout the specification.

In the drawings, thicknesses of various layers and regions are exaggerated for clarity. Further, in the drawings, thicknesses of partial layers and regions are exaggerated for convenience of explanation.

As used herein, when any component is formed on an upper (or lower) part of a surface, it means not only that any component is formed in contact with an upper (or lower) part of a surface, but also that there is no other component between the any surface and any component formed on (or under) the any surface.

Figure 1:
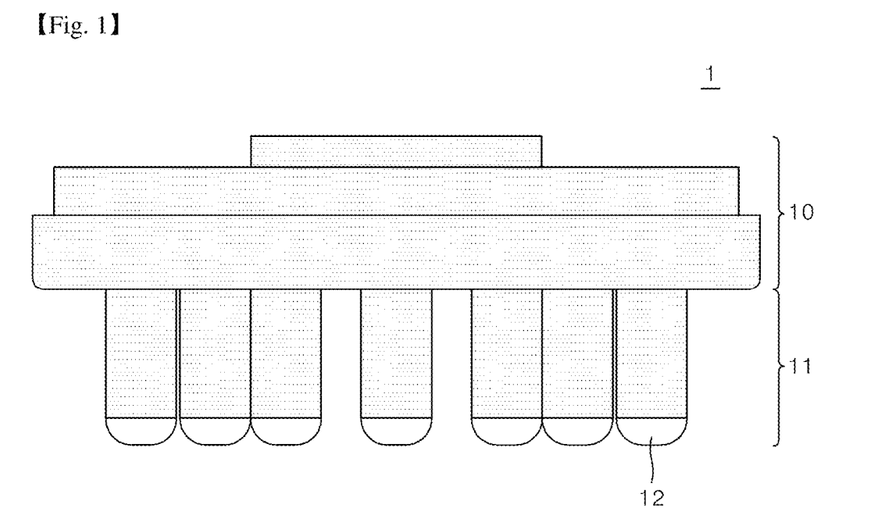
FIG. 1 is a cross-sectional view of a dry electrode for detecting a bio-signal according to an embodiment of the present disclosure.

Now, referring to FIG. 1, described is a dry electrode 1 for detecting a bio-signal according to an embodiment of the present disclosure. FIG. 1 is a cross-sectional view of a dry electrode 1 for detecting a bio-signal according to an embodiment of the present disclosure.

The dry electrode 1 for detecting a bio-signal may include a body part 10; a protrusion part 11 formed on one surface of the body part 10; and a coating part 12 formed on an end surface of the protrusion part 10, wherein the body part 10 and the protrusion part 11 may include a conductive silicone, and the coating part 12 may include Ag and AgCl.

As shown in FIG. 1, the end surface of the protrusion part 11 may be formed with a convex curved surface in the protruding direction of the protrusion part 11.

The protrusion part 11 are formed with a plurality of columns or spikes, and formed along a lattice, honeycomb, or spiral arrangement, or the protruding portion 11 may be formed with an integrated lattice, honeycomb, or spiral shape as a whole.

The dry electrode 1 for detecting a bio-signal can be applied to a device for detecting the bio-signal. The device can detect a bio-signal such as an Electroencephalogram (EEG), an electrocardiogram (ECG), and an Electromyogram (EMG) through the dry electrode 1 for detecting a bio-signal. For example, the device for detecting a bio-signal is a medical device, and can monitor disease states such as dementia or depression by detecting brainwaves different from that of a normal human being. A specific example of the medical device to which the dry electrode 1 for detecting a bio-signal can be applied is transcranial direct current stimulation (tDCS) which applies a direct current to the subject's head.

The dry electrode 1 for detecting a bio-signal applied to the device for detecting a bio-signal used for a brainwave detecting technology or a brain electrical stimulation technology may be attached to the user's head.

The device for detecting a bio-signal that detects brainwaves can detect brainwaves (AC) flowing in a brain at a voltage level. Specifically, when the brainwaves are transmitted to the dry electrode 1 for detecting a bio-signal, the body part 10 and the protrusion part 11 can transmit an electrical stimulation because the main component is a conductive silicone which is a conductive material.

The dry electrode 1 for detecting a bio-signal may further include a conductive wire inserted into the body part 10 to transmit brainwaves to the body part of the device for detecting a bio-signal.

A conductive silicone, which is a conductive material forming the body part 10 and the protrusion part 11, may specifically include, but is not limited to, one selected from the group consisting of a silicone compound having a vinyl group or a hydroxyl group, a siloxane compound having a terminal vinyl group or a terminal hydroxyl group, and combinations thereof.

The conductive silicone includes a first silicone-based compound and carbon black.

The first silicone-based compound may include one selected from the group consisting of a silicone compound having a vinyl group or a hydroxyl group, a siloxane compound having a terminal vinyl group or a terminal hydroxyl group, and combinations thereof.

The carbon black acts as a conductive filler and allows the first silicone-based compound to exhibit a conductive characteristic so that current can flow through the conductive silicone in the body part 10 and the protrusion part 11.

Specifically, the conductive silicone may include about 40 parts to about 80 parts by weight of carbon black relative to 100 parts by weight of the first silicone-based compound. Although high content of carbon black can improve the electrical conductivity, carbon black having certain limits or higher may cause agglomeration, making it impossible to obtain a uniform composition with other components, and also lowering the adhesive strength. Therefore, carbon black having the above described range of contents can appropriately secure the adhesive strength characteristic while imparting an appropriate electrical conductivity characteristic.

The coating part 12 may further include, in addition to Ag and AgCl, a binder resin and a second silicone-based compound to form a coating layer.

The binder resin may be a resin that can be cured by thermal curing.

Specifically, the binder resin may include one selected from the group consisting of an epoxy resin, a polyester resin, a polyimide resin, a silicone resin, a urethane resin, a vinyl resin, and combinations thereof. The binder resin having Ag and AgCl may be used in a predetermined amount to form a coating layer of the coating part 12.

The second silicone-based compound may specifically include one selected from the group consisting of a silicone compound, a siloxane compound, and combinations thereof, and the silicone compound and the siloxane compound of the second silicone-based compound may be a compound terminated with a vinyl group or a hydroxyl group. For example, materials used for the conductive silicone may be used in the same manner. The second silicone-based compound may be included in an amount of less than about 10% by weight of the coating part 12.

In one embodiment of the present disclosure, the coating part may further include 3-aminopropyltriethoxysilane.

When the coating part includes Ag, AgCl, and 3-aminopropyltriethoxysilane, the conductive silicone included in the body part 10 and the protrusion part 11 includes a first silicone-based compound and carbon black.

The first silicone-based compound may include one selected from the group consisting of a hydroxyl group-containing silicone compound, a hydroxyl group-containing siloxane compound, and combinations thereof.

When the coating part includes Ag, AgCl, and 3-aminopropyltriethoxysilane, the carbon black acts as conductive filler and allows the first silicone-based compound to exhibit a conductive characteristic so that current can flow through the conductive silicone in the body part 10 and the protrusion part 11.

When the coating part includes Ag, AgCl, and 3-aminopropyltriethoxysilane, specifically, the conductive silicone may include about 40 parts to about 80 parts by weight of carbon black relative to 100 parts by weight of the first silicone-based compound. The higher content of carbon black can improve the electrical conductivity, but carbon black with a certain limit or more may cause agglomeration, making it impossible to obtain a uniform composition with other composition, and also lowering the adhesive strength. Therefore, the carbon black having the above range of content can appropriately secure the adhesive strength characteristic while imparting appropriate electrical conductivity characteristics.

The protrusion part 11 may have a height that can be appropriately adjusted according to the application. Specifically, the protrusion part 11 may have a height of about 3.0 mm to about 9.0 mm, but is not limited thereto. When the protrusion part 11 has too small a height, for example, the hair on the head may be smaller than the thickness of the covered part when contacted with the head for the measurement of brainwaves, and contact with the head may be difficult; on the contrary, when the protrusion part has too large a height, the protrusion part do not have sufficient strength to pierce the hair-covered part, and can bend at the surface of the hair to make it also difficult to contact with the head. If the hair does not contact the head and comes in contact with only the hair, it will be difficult to measure brainwaves because the hair is nonconductive. Therefore, the protrusion part 11 having the height of the above range is suitable for the measurement of brainwaves.

Bio-potential is a flow of ions, and the flow of these ions is transduced into electrons to detect the brainwaves. For example, when the dry electrode 1 for detecting a bio-signal comes into contact with the head, a contact potential is formed at the interface between the head. The quality of the signal is determined by the contact potential thus formed and the capacitance component of the dry electrode 1 for detecting a bio-signal. That is, as the contact potential difference and the capacitance component are lower, a constant signal can be read.

The coating part 12 includes Ag, AgCl, and, optionally, 3-aminopropyltriethoxysilane, which are materials having a low contact potential difference and a low capacitance component.

An ion channel is formed by Cl⁻ (electrolyte) in Ag and AgCl contained in the coating part 12, so that a bio-signal, that is, an ion current can be effectively detected.

As such, the coating part 12 uses a material having a low capacitance and impedance so as to prevent distortion of the bio-signal. The dry electrode 1 for detecting a bio-signal does not need to form a separate ion channel by forming the coating part 12, thereby eliminating the need to use a patch.

Further, when the coating part 12 includes 3-aminopropyltriethoxysilane, the 3-aminopropyltriethoxysilane forms a chemical bond by chemical reaction with the first silicone-based compound in the conductive silicone in the protrusion parts 11, thereby additionally enhancing the coating adhesion with the protrusion part.

The coating part 12 may have a coating thickness of from about 10 microns to about 1000 microns, specifically, from about 100 microns to about 500 microns. When the coating part 12 has a thinner thickness, durability and reliability are low, whereas when the coating part 12 is too thick, the impedance becomes large. In this regard, the coating part 12 may have a thickness in the above-described range to provide appropriate durability and reliability while lowering the impedance.

When the coating part includes Ag, AgCl, and 3-aminopropyltriethoxysilane, the coating part 12 may further include, in addition to Ag and AgCl, a binder resin and a second silicone-based compound to form a coating layer.

When the coating part includes Ag, AgCl, and 3-aminopropyltriethoxysilane, the binder resin may be a resin that can be cured by thermal curing. Specifically, the binder resin may include one selected from the group consisting of an epoxy resin, a polyester resin, a polyimide resin, a silicone resin, a urethane resin, a vinyl resin, and combinations thereof. The binder resin may be used in a predetermined amount to form a coating layer of the coating part 12 including Ag, AgCl and 3-aminopropyltriethoxysilane.

When the coating part includes Ag, AgCl, and 3-aminopropyltriethoxysilane, the second silicone-based compound may include one selected from the group consisting of a hydroxyl group-containing silicone compound, a hydroxyl group-containing siloxane compound, and combinations thereof. When the coating part includes Ag, AgCl, and 3-aminopropyltriethoxysilane, materials used for the first silicone-based compound of the conductive silicone, for example, may be used in the same manner. When the coating part includes Ag, AgCl, and 3-aminopropyltriethoxysilane, the second silicone-based compound may be included in an amount of less than about 10% by weight in the coating part 12.

When the coating part includes Ag, AgCl, and 3-aminopropyltriethoxysilane, a coating composition for forming the coating part 12 includes 3-aminopropyltriethoxysilane. The coating composition is applied according to a known method such as dip coating, electroplating, spray coating, or vapor deposition coating to form the coating part 12. Then, the ethoxy groups in the 3-aminopropyltriethoxysilane is connected to the second silicone-based compound in the coating part 12 by a condensation reaction to form a network structure. In addition, the ethoxy groups in the 3-aminopropyltriethoxysilane in contact with the interface with the end of the protrusion part is chemically bonded to the first silicone-based compound of the conductive silicone contained in the protrusion part by a condensation reaction When the coating part includes Ag, AgCl, and 3-aminopropyltriethoxysilane, both the first silicone-based compound and the second silicone-based compound include hydroxyl groups. Then, these hydroxyl groups and the ethoxy groups in the 3-aminopropyltriethoxysilane can be connected by a condensation reaction.

When the coating part includes Ag, AgCl, and 3-aminopropyltriethoxysilane, the coating part 12 may have a total Ag and AgCl content of about 60% to about 95% by weight. The coating part 12 includes Ag and AgCl in the above-described contents. Then, when the dry electrode 1 for detecting a bio-signal detects a bio-signal, it is possible to ensure proper conductivity and at the same time to minimize the occurrence of noise in the bio-signal.

Further, when the coating part includes Ag, AgCl, and, optionally, 3-aminopropyltriethoxysilane, in the coating part 12, the weight ratio of Ag to AgCl may be about 50:50 to about 95:5. The AgCl can be adjusted relative to Ag within the above-described contents. Then, when the dry electrode 1 for detecting a bio-signal detects a bio-signal, it is possible to ensure proper conductivity and at the same time to minimize the occurrence of noise in the bio-signal.

When the coating part includes Ag, AgCl, and 3-aminopropyltriethoxysilane, the coating part 12 may include from about 0.1% to about 10% by weight of 3-aminopropyltriethoxysilane. When the coating part 12 includes a higher content of 3-aminopropyltriethoxysilane more than about 10% by weight, unreacted 3-aminopropyltriethoxysilane fails to conduct a condensation reaction with the silicone compound, and may cause coating defects.

The dry electrode 1 for detecting a bio-signal may further include a nonconductive cover formed on a surface other than a surface of the body part 10 on which the protrusion part 11 is formed. The user may hold the dry electrode 1 for detecting a bio-signal by bringing the nonconductive cover into contact with the hand. Then, the dry electrode 1 for detecting a bio-signal can be safely used.

In another embodiment of the present disclosure, there is provided a method of preparing a dry electrode 1 for detecting a bio-signal, including the steps of: forming a body part 10 having a protrusion part 11 on one surface thereof to include a conductive silicone; and coating an end surface of the protrusion part 11 including Ag, AgCl, and, optionally, 3-aminopropyltriethoxysilane to form a coating part 12.

A dry electrode 1 for detecting a bio-signal described above can be prepared according to the method of preparing the dry electrode 1 for detecting a bio-signal. Therefore, detailed description of the dry electrode 1 for detecting a bio-signal prepared according to the method of preparing the dry electrode 1 for detecting the bio-signal is as described above.

The body part 10 includes a protrusion part 11 on one surface thereof, which may be prepared by providing a silicone conductive composition containing a conductive silicone, i.e., a first silicone-based compound and carbon black, and then molding the silicone conductive composition. The method of molding the body part 10 having the protrusion part 11 on one surface thereof can be performed according to a known method, but is not particularly limited.

When the coating part includes Ag and AgCl, the silicone conductive composition for forming a body part 10 having a protrusion part 11 on one surface thereof may include, as a conductive silicone, a first silicone-based compound containing one selected from the group consisting of a vinyl group- or a hydroxyl group-terminated silicone compound, a vinyl group- or a hydroxyl group-terminated siloxane compound, and combinations thereof; and carbon black.

When the coating part includes Ag, AgCl, and 3-aminopropyltriethoxysilane, the silicone conductive composition for forming a body part 10 having a protrusion part 11 on one surface thereof may include as a conductive silicone a first silicone-based compound containing one selected from the group consisting of a hydroxyl group-containing silicone compound, a hydroxyl group-containing siloxane compound, and combinations thereof; and carbon black.

The silicone conductive composition for forming a body part 10 having a protrusion part 11 on one surface thereof may include about 40 parts to about 80 parts by weight of carbon black relative to 100 parts by weight of the conductive silicone.

The step of coating the coating part 12 containing Ag, AgCl, and, optionally, 3-aminopropyltriethoxysilane on the end surface of the protrusion part 11 may be performed by, for example, dip coating, electroplating, spray coating, and vapor deposition coating.

When a dip coating method is used to form the coating part 12 on one end surface of the protrusion part 11, first, a binder resin, a second silicone-based compound, an Ag powder, an AgCl powder, optionally 3-aminopropyltriethoxysilane, and a solvent are mixed to prepare a coating composition, and then the protrusion part 11 may be formed by dipping an end surface in the form of protrusion part extending from the body part 10 into the coating composition and thermosetting it.

Details of the binder resin and the second silicone-based compound are as described above.

The content of Ag and AgCl in the coating composition can be adjusted by adjusting the content of Ag and AgCl in the coating part 12 to be about 60% to about 95% by weight.

In addition, when the coating part includes Ag, AgCl, and 3-aminopropyltriethoxysilane, the coating composition may include from about 0.1% to about 10% by weight of 3-aminopropyltriethoxysilane based on the solids of the composition.

The weight ratio of Ag to AgCl in the coating composition may be from about 50:50 to about 95:5.

The thermosetting may be performed at about 80° C. to about 200° C. The thermosetting may be performed in the above temperature range to form the coating part 12 having a desired thickness. When the thermosetting is carried out, the second silicone-based compound may form a network structure during thermosetting, and 3-aminopropyltriethoxysilane may together therewith form a network structure as described above. Further, as described above, when the coating part includes Ag, AgCl, and 3-aminopropyltriethoxysilane, 3-aminopropyltriethoxysilane in contact with the interface with the end surface of the protrusion part 11 during the thermosetting can be chemically bonded with the first silicone-based compound in the protrusion part 11 by a condensation reaction.

The time for performing the thermosetting may be appropriately adjusted depending on the application and the desired physical properties. For example, when forming the above-described coating part 12 having a thickness of about 10 µm to about 1000 µm, this can be performed for about 1 minute to about 150 minutes at the above temperature range.

The coating part 12 may be formed by dipping once and curing once, or may be formed by repeating these twice or more. For example, the coating part 12 may be formed to have a thickness of about 150 µm, which may then be repeated twice to form a coating part 12 to have a total thickness of 450 µm.

The thickness of the coating part 12 may be formed by controlling the viscosity of the coating composition. Specifically, the coating composition may have a viscosity ranging from about 20,000 cps to about 25,000 cps at about 25° C. Using the coating composition having a viscosity in the above range, the above-described coating part 12 having a thickness of about 100 µm to about 500 µm described above can be formed and even formed to have a thickness greater than those range.

The viscosity of the coating composition can be suitably controlled by the content of the solvent. The total content of Ag and AgCl in the coating composition may be in the range of about 50% to about 95% by weight to have a viscosity in the above range.

Hereinafter, Examples and Comparative Examples of the present disclosure will be described. However, it should be noted that while the preferred examples are listed for easy understanding of the contents of the present disclosure, the present disclosure is not limited to these examples.

EXAMPLES

Example 1

First, conductive silicone (trade name: SH6570U, manufacturer: KCC, comprising 100 parts by weight of a first silicone-based compound and 50 parts by weight of carbon black) was prepared. As shown in FIG. 1, a body part having protrusion parts on one surface thereof was molded using the conductive silicone.

Separately, 63 parts by weight of Ag and AgCl mixed powder (wherein Ag:AgCl weight ratio in Ag and AgCl mixed powder is 82:18), 7.8 parts by weight of decamethyltetrasiloxane, and 11.8 parts by weight of epoxy resin were mixed with 17.4 parts by weight of a mixed solvent of xylene, toluene and ethylbenzene, to which methyl ethyl ketone (MEK) was added to prepare a coating composition having a viscosity of 20,000 cP at 25° C. Then, 3-aminopropyltriethoxysilane was added in an amount of 2% by weight in the coating composition.

The end surface of the protrusion parts was dipped in the coating composition and then thermoset at 100° C. for 2 hours to prepare a dry electrode for detecting a bio-signal in which a coating having a thickness of 150 µm was formed on the end surface of the protrusion parts.

Example 2

A dry electrode for detecting a bio-signal was prepared in the same manner as in Example 1, except that the Ag:AgCl weight ratio of the Ag and AgCl mixed powders in the coating composition for forming the coating in Example 1 was 70:30.

Example 3

A dry electrode for detecting a bio-signal was prepared in the same manner as in Example 1, except that the Ag:AgCl weight ratio of the Ag and AgCl mixed powders in the coating composition for forming the coating in Example 1 was 70:30, and the 3-aminopropyltriethoxysilane has content of 4% by weight in the coating composition.

Example 4

A dry electrode for detecting a bio-signal was prepared in the same manner as in Example 1, except that the coating composition was prepared without adding 3-aminopropyltriethoxysilane to form the coating part.

Example 5

A dry electrode for detecting a bio-signal was prepared in the same manner as in Example 2, except that the coating composition was prepared without adding 3-aminopropyltriethoxysilane to form the coating part.

Comparative Example 1

A dry electrode for detecting a bio-signal was prepared without forming a coating in Example 1.

Experiment 1

Figure 2:
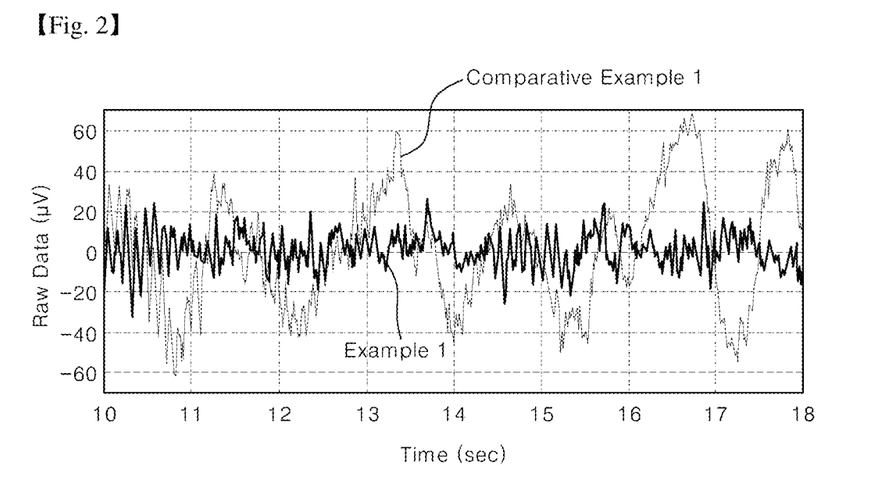
FIG. 2 is a graph showing time-dependent brainwaves measured using a dry electrode for detecting a bio-signal prepared from Example 1 and Comparative Example 1.

FIG. 2 is a graph showing time-dependent brainwaves measured using a dry electrode for detecting a bio-signal prepared from Example 1 and Comparative Example 1.

In FIG. 2, Example 1 is a green line, and Comparative Example 1 is a blue line. It can be predicted from Comparative Example 1 that the signal has large amplitude to include noise. On the other hand, it can be confirmed from Example 1 that the signal has not so large amplitude and the noise is not severe and therefore the brainwaves are well detected.

Experiment 2

For Examples 1, 2, 4 and 5, the adhesion between the protrusion parts and the coating part was evaluated.

An adhesive tape (trade name: #396 tape, manufactured by 3M) was attached to the coating part of the dry electrodes for detecting a bio-signal in Examples 1 and 4, and then immediately peeled off.

Figure 3:
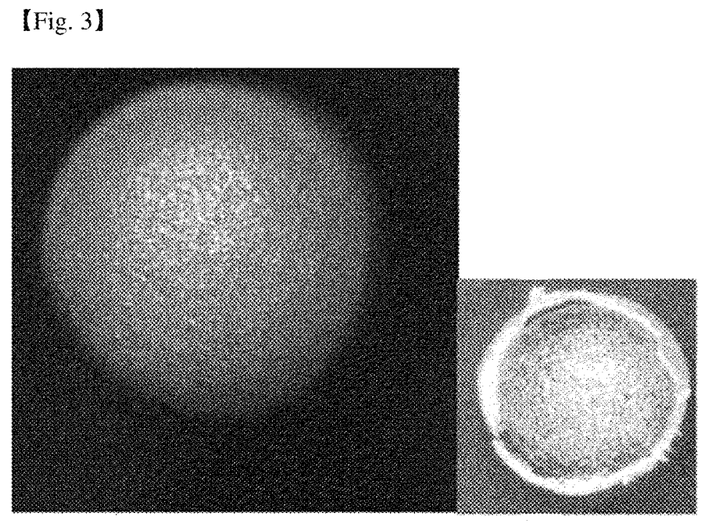
FIG. 3 is a photograph obtained after removing an adhesive tape in Example 1.

FIG. 3 is a photograph obtained after removing an adhesive tape in Example 1.

Figure 4:
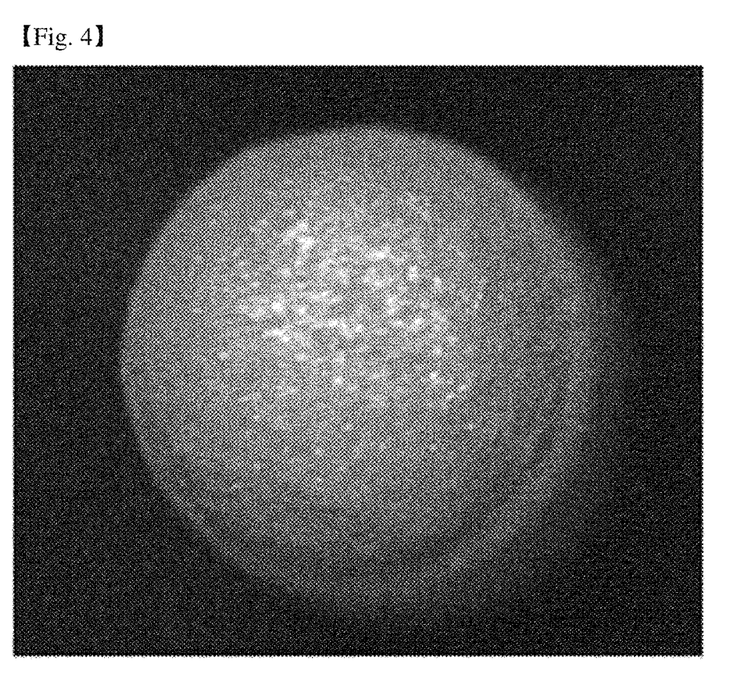
FIG. 4 is a photograph obtained after removing an adhesive tape in Example 2.

FIG. 4 is a photograph obtained after removing an adhesive tape in Example 2.

Figure 5:
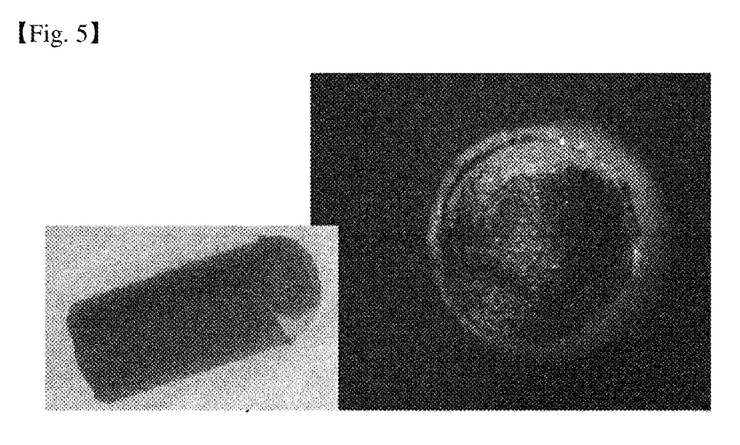
FIG. 5 is a photograph obtained after removing an adhesive tape in Comparative Example 2.

FIG. 5 is a photograph obtained after removing an adhesive tape in Example 4.

Figure 6:
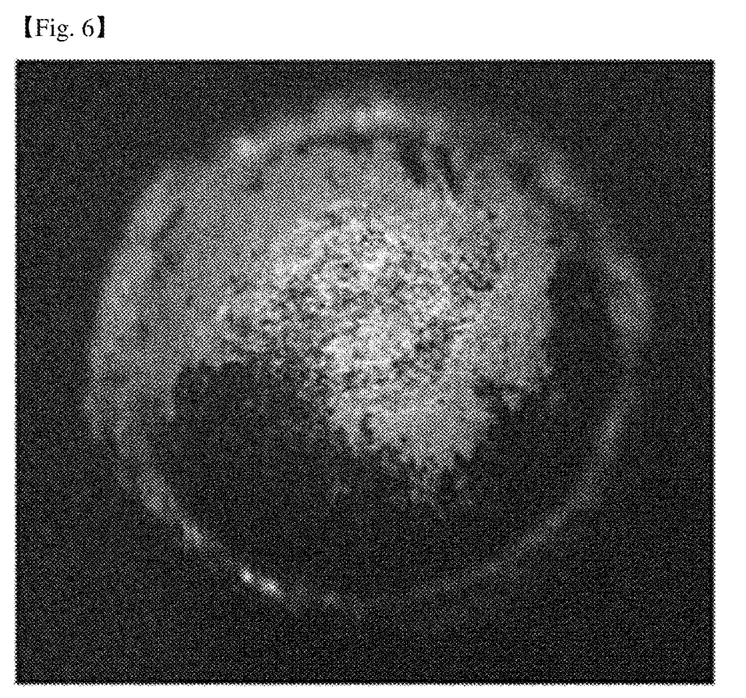
FIG. 6 is a photograph obtained after removing an adhesive tape in Comparative Example 3.

FIG. 6 is a photograph obtained after removing an adhesive tape in Example 5.

Referring to FIGS. 3 and 4, for Examples 1 and 2, the coating part was not delaminated from the protrusion parts at all. On the other hand, referring to FIGS. 5 and 6, for Examples 4 and 5, the coating part was delaminated from the protrusion parts and transferred to the adhesive tape.

The above results confirm us that in Examples 1 and 2 comprising 3-aminopropyltriethoxysilane, the adhesion between the coating part and the protrusion part was greatly improved.

Experiment 3

For Examples 2, 3 and 5, the adhesion between the protrusion part and the coating part was evaluated using a testing apparatus (model name: ESM301, manufactured by Mark-10).

The 180 degrees peel test for the coating in the dry electrodes for detecting a bio-signal according to Examples 2, 3 and 5 was performed using the above apparatus and the adhesion was evaluated by measuring the strength as delaminated. The evaluation results are shown in Table 1 below.

TABLE 1

| Division | Adhesive strength (180 degrees delamination strength) [gf/cm] |
|---|---|
| Ex. 2 | 225.90 |
| Ex. 3 | 254.11 |
| Ex. 5 | 34 |

It can be seen that the adhesive strength in Examples 2 and 3 is far superior to that of Example 5 without 3-aminopropyltriethoxysilane, and further, the adhesive strength in Example 3 having a higher content of 3-aminopropyltriethoxysilane was even better.

While the preferred examples of the disclosure have been shown and described for illustrative purpose only, it should be understood that various substitutions, modifications and variations may be made by those skilled in the art without departing from the spirit or scope of the disclosure. Accordingly, all such modifications and variations are included in the scope of the disclosure as defined by the following claims.

DESCRIPTION OF SYMBOLS

1: dry electrode for detecting a bio-signal
10: body part
11: protrusion part
12: coating part

The invention claimed is:

1. A dry electrode for detecting a bio-signal, comprising:
a body part;
a protrusion part on one surface of the body part; and
a coating part on an end surface of the protrusion part, wherein the coating part comprises Ag and AgCl,
wherein the body part and the protrusion part comprise a conductive silicone, and the conductive silicone comprises a first silicone-based compound and carbon black, and
wherein the coating part further comprises 3-aminopropyltriethoxysilane.

2. The dry electrode for detecting a bio-signal of claim 1, wherein the end surface of the protrusion part is formed into a convex curved surface in the protruding direction of the protrusion part.

3. The dry electrode for detecting a bio-signal of claim 1, wherein the first silicone-based compound comprises one selected from the group consisting of a vinyl group- or a hydroxyl group-terminated silicone compound, a vinyl group- or a hydroxyl group-terminated siloxane, and combinations thereof.

4. The dry electrode for detecting a bio-signal of claim 1, wherein the first silicone-based compound comprises one selected from the group consisting of a hydroxyl group-containing silicone compound, a hydroxyl group-containing siloxane compound, and combinations thereof.

5. The dry electrode for detecting a bio-signal of claim 3, wherein the conductive silicone comprises 40 parts to 80 parts by weight of carbon black relative to 100 parts by weight of the first silicone-based compound.

6. The dry electrode for detecting a bio-signal of claim 1, wherein the protrusion part has a height in the range of 3.0 mm to 9.0 mm.

7. The dry electrode for detecting a bio-signal of claim 1, wherein the coating part has a thickness of 10 μm to 1000 μm.

8. The dry electrode for detecting a bio-signal of claim 1, wherein the coating part further comprises a binder resin and a second silicone-based compound.

9. The dry electrode for detecting a bio-signal of claim 1, wherein the coating part further comprises a binder resin and a second silicone-based compound, and the 3-aminopropyltriethoxysilane is connected to the second silicone-based compound by a condensation reaction to form a network structure.

10. The dry electrode for detecting a bio-signal of claim 1, wherein the 3-aminopropyltriethoxysilane in the coating part is chemically bonded with the first silicone-based compound in the protrusion part by a condensation reaction.

11. The dry electrode for detecting a bio-signal of claim 8, wherein the binder resin comprises one selected from the group consisting of an epoxy resin, a polyester resin, a polyimide resin, a silicone resin, a urethane resin, a vinyl resin, and combinations thereof.

12. The dry electrode for detecting a bio-signal of claim 1, wherein the coating part further comprises a binder resin and a second silicone-based compound, and the second silicone-based compound comprises one selected from the group consisting of a silicone compound, a siloxane compound, and combinations thereof.

13. The dry electrode for detecting a bio-signal of claim 1, wherein the coating part further comprises a binder resin and a second silicone-based compound, and the second silicone-based compound comprises one selected from the group consisting of a hydroxyl group-containing silicone compound, a hydroxyl group-containing siloxane compound, and combinations thereof.

14. The dry electrode for detecting a bio-signal of claim 1, wherein, in the coating part, the weight ratio of Ag to AgCl is 50:50 to 95:5.

15. The dry electrode for detecting a bio-signal of claim 1, wherein the coating part comprises 0.1% to 10% by weight of 3-aminopropyltriethoxysilane.

16. The dry electrode for detecting a bio-signal of claim 1, wherein the protrusion part is formed with a plurality of columns or spikes, and formed along a lattice, honeycomb, or spiral arrangement, or the protrusion part is formed with an integrated lattice, honeycomb, or spiral shape as a whole.

17. A method of manufacturing a dry electrode for detecting a bio-signal, comprising:
    forming a body part having a protrusion part on one surface thereof, wherein the body part and the protrusion part comprises a conductive silicone, and wherein the conductive silicone comprises a first silicone-based compound and carbon black; and
    coating an end surface of the protrusion part to form a coating part comprising Ag and AgCl,
    wherein the coating part further comprises 3-aminopropyltriethoxysilane.

18. The method of manufacturing a dry electrode for detecting a bio-signal of claim 17, wherein coating the end surface of the protrusion part to form the coating part comprises:
    mixing a binder resin, an Ag powder, an AgCl powder, and a solvent to prepare a coating composition, wherein the end surface of the protrusion part is dipped into the coating composition and is thermally cured to form the coating part, or
    coating the end surface of the protrusion part with the coating part by electroplating, spray coating or vapor deposition coating.

19. The method of manufacturing a dry electrode for detecting a bio-signal of claim 18, wherein the coating composition has a viscosity in the range of from 20,000 cps to 25,000 cps at 25° C.

* * * * *